US006184991B1

(12) United States Patent
Soto et al.

(10) Patent No.: US 6,184,991 B1
(45) Date of Patent: Feb. 6, 2001

(54) APPARATUS AND METHOD OF MEASURING DRY TIME OF PRINTING COMPOSITION

(75) Inventors: Braulio Soto, LaCenter; Stephen P. Stemple, Vancouver, both of WA (US)

(73) Assignee: Hewlett-Packard, Palo Alto, CA (US)

( * ) Notice: Under 35 U.S.C. 154(b), the term of this patent shall be extended for 0 days.

(21) Appl. No.: 09/294,772

(22) Filed: Apr. 19, 1999

(51) Int. Cl.$^7$ .................................................. G01N 21/47
(52) U.S. Cl. .......................................................... 356/446
(58) Field of Search ................................... 356/446, 379, 356/380, 447, 448; 347/6, 14, 19, 81, 100, 107; 400/56, 126; 73/149, 861.41

(56) References Cited

U.S. PATENT DOCUMENTS

| | | |
|---|---|---|
| 4,617,580 | 10/1986 | Miyakawa .............................. 346/136 |
| 5,078,497 | 1/1992 | Borton et al. ......................... 356/446 |
| 5,160,981 | 11/1992 | Hirashima ............................. 356/446 |
| 5,387,976 | 2/1995 | Lesniak ................................. 356/379 |
| 5,774,146 | 6/1998 | Mizutani ................................. 347/43 |

FOREIGN PATENT DOCUMENTS

| | | |
|---|---|---|
| 57-172235 | 10/1982 | (JP) . |
| 02196944 | 8/1990 | (JP) . |

OTHER PUBLICATIONS

Patent Abstract of Japan, Publication No. 05264441; Published on Oct. 12, 1993; Niigata Denki KK.
Patent Abstract of Japan, Publication No. 08297022; Published on Nov. 12, 1996;Mitsubishi Electric Corp.
Patent Abstract of Japan, Publication No. 08159957; Published on Jun. 21, 1996, Chino Corp.
UK Patent Application GB 2 178 843 A, published Feb. 18, 1987.
UK Patent Office Search Report dated Jun. 12, 2000, for related UK patent application 0008520.9 filed Apr. 6, 2000.

*Primary Examiner*—Frank G. Font
*Assistant Examiner*—Michael P. Stafira
(74) *Attorney, Agent, or Firm*—Erik A. Anderson

(57) ABSTRACT

A detection system for measuring a dry time of a printing composition used by a printing device is disclosed. An embodiment of the detection system includes a source, a sensor, and a controller. The source is configured to transmit a first light signal toward a quantity of printing composition deposited on a print medium. A sensor is configured to detect a second light signal reflected by the printing composition in response to illumination by the first light signal, the second light signal having a magnitude that decreases to a substantially constant value as the printing composition dries over a period of time. The sensor is also configured to convert the second light signal into an electrical signal having a value proportional to the magnitude of the second light signal. The controller is coupled to the sensor and configured to receive the electrical signal from the sensor over the period of time the printing composition dries. The controller is also configured to determine a dry time for the printing composition based upon the electrical signal. A printing device including the detection system is also disclosed. A method of measuring a dry time of a printing composition used by a printing device is additionally disclosed. Further characteristics and features of the detection system, printing device, and method are described herein, as are examples of various alternative embodiments.

15 Claims, 3 Drawing Sheets

APPARATUS AND METHOD OF MEASURING DRY TIME OF PRINTING COMPOSITION

BACKGROUND AND SUMMARY

The present invention relates to printing devices. More particularly, the present invention relates to an apparatus and method of measuring dry time of printing composition.

Printing devices, such as inkjet printers and laser printers, use printing composition (e.g., ink or toner) to print text, graphics, images, etc. onto print media. Inkjet printers may use print cartridges, also known as "pens", which shoot drops of printing composition, referred to generally herein as "ink", onto a print medium such as paper or transparencies. Each pen has a printhead that includes a plurality of nozzles. Each nozzle has an orifice through which the ink drops are fired. To print an image, the printhead is propelled back and forth across the page by, for example, a carriage, while shooting drops of ink in a desired pattern as the printhead moves. The particular ink ejection mechanism within the printhead may take on a variety of different forms known to those skilled in the art, such as thermal printhead technology. For thermal printheads, the ink may be a liquid, where dissolved colorants or pigments are dispersed in a solvent.

In a current thermal system, a barrier layer containing ink channels and vaporization chambers is located between an orifice plate and a substrate layer. This substrate layer typically contains linear arrays of heating elements, such as resistors, which are energized to heat ink within the vaporization chambers. Upon heating, the ink in the vaporization chamber turns into a gaseous state and forces or ejects an ink drop from a orifice associated with the energized resistor. By selectively energizing the resistors as the printhead moves across the print medium, the ink is expelled in a pattern onto the print medium to form a desired image (e.g., picture, chart or text).

In order for the image to be fixed to the print media so that it will not smear, the ink must be dried. The ink is dried by a combination of the solvent evaporating and the solvent absorbing into the print medium, both of which take time. Various factors control the amount of time required for a particular ink to dry. These factors include the type of print media, the quantity of solvent in an ink, the amount of ink on the print media, and ambient temperature and humidity. To reduce the amount of this time, the surface of some types of print media may be specially coated to help speed drying. Other means may also be used such as special chemicals generally know as "fixers" that are applied to print media before or after printing. Various types of heating devices may also be used to heat print media before and/or after printing.

Irrespective of how drying is accomplished, it is useful to know printing composition dry time for a particular combination of printing composition, print medium, printing device, and ambient conditions. Such information can be used by a printing device to help prevent image smear, print media cockle (print media buckle toward a printhead), and print media curl (curling along at least one edge of a print media), as well as help maximize printing device throughput.

Accordingly, the present invention is directed to measuring printing composition dry time to help prevent the above-described problems and optimize printing. The present invention accomplishes this without degrading output print quality of a printing device.

An embodiment of a detection system in accordance with the present invention for measuring a dry time of a printing composition used by a printing device includes a source, a sensor, and a controller. The source is configured to transmit a first light signal toward a quantity of printing composition deposited on a print medium. The printing composition reflects a second light signal in response to illumination by the first light signal. The second light signal has a magnitude that decreases to a substantially constant value as the printing composition dries over a period of time. The sensor is configured to detect the second light signal and convert the second light signal into an electrical signal having a value proportional to the magnitude of the second light signal. The controller is coupled to the sensor and is configured to receive the electrical signal from the sensor over the period of time the printing composition dries. The controller is also configured to determine a dry time for the printing composition based upon the electrical signal.

The above-described embodiment of a detection system of the present invention may be modified and include the following characteristics described below. The controller may be further configured to adjust an operating parameter of the printing device based upon the determined dry time. The source may include a light emitting diode and the sensor may include a photodiode. The print media detection system may be used in a printing device.

An alternative embodiment of a detection system in accordance with the present invention for measuring a dry time of a printing composition used in a printing device includes structure for illuminating a printing composition subsequent to deposition on a print medium. The detection system also includes structure for measuring over a selected period of time a quantity of light reflected by the printing composition subsequent to illumination. The detection system further includes structure for determining a dry time for the printing composition based upon the measured quantity of light reflected by the printing composition over the selected period of time.

The above-described alternative embodiment of a detection system of the present invention may be modified and include the following characteristics described below. The detection system may further include structure for adjusting at least one operating parameter of a printing device based upon the dry time. The detection system may further include structure for depositing the printing composition on the print medium. In such cases, the depositing structure may include an inkjet printhead. The detection system may be used in a printing device.

An embodiment of a method in accordance with the present invention of measuring a dry time of a printing composition used by a printing device includes depositing a quantity of printing composition onto a print medium and illuminating the printing composition subsequent to printing. The method additionally includes measuring over a selected period of time a quantity of light reflected by the printing composition in response to illuminating. The method further includes determining a dry time for the printing composition based upon the measured quantity of light reflected by the printing composition over the selected period of time.

The above-described embodiment of a method of the present invention may be modified and include the following characteristics described below. Depositing may include placing a plurality of drops of printing composition onto the print medium. Depositing may include selecting a number of drops of printing composition to place onto the print medium. Each of the drops may have a volume substantially equal to a selected volume.

The method may additionally include adjusting at least one operating parameter of a printing device based upon the determined dry time. Illuminating and measuring may include optically scanning the printing composition. The method may be used in a printing device.

Other objects, advantages, and novel features of the present invention will become apparent from the following detailed description of the invention when considered in conjunction with the accompanying drawings.

DETAILED DESCRIPTION OF THE DRAWINGS

Figure 1:
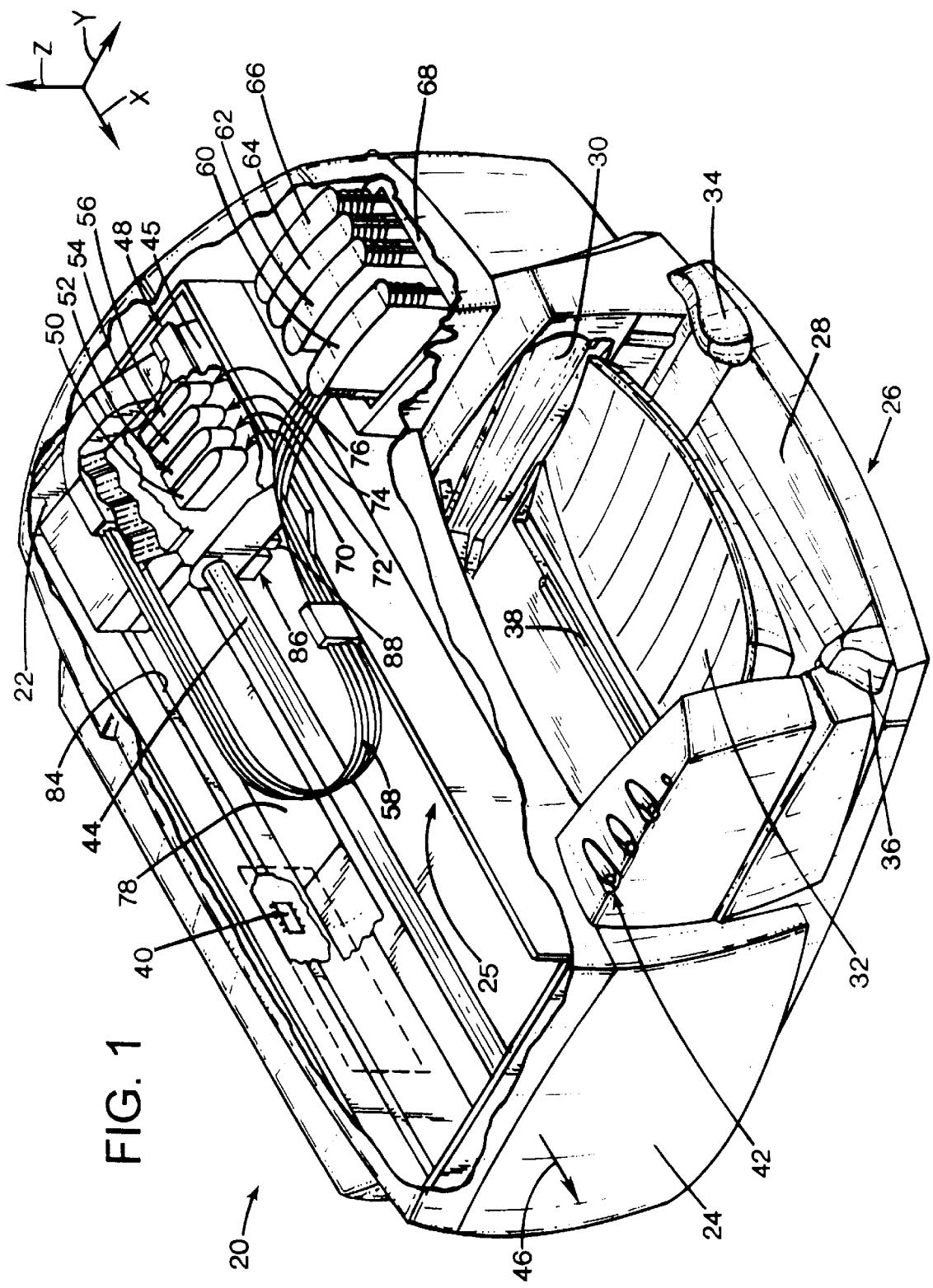
FIG. 1 is a front perspective view of a printing device that includes an embodiment of the present invention.

FIG. 1 illustrates an embodiment of an inkjet printing device 20, here shown as an "off-axis" inkjet printer, constructed in accordance with the present invention, which may be used for printing business reports, correspondence, desktop publishing, and the like, in an industrial, office, home or other environment. A variety of inkjet printing devices are commercially available. For instance, some of the printing devices that may embody the present invention include plotters, portable printing units, copiers, cameras, video printers, and facsimile machines, to name a few, as well as various combination devices, such as a combination facsimile and printer. For convenience, the concepts of the present invention are illustrated in the environment of inkjet printer 20.

While it is apparent that the printing device components may vary from model to model, the typical inkjet printer 20 includes a frame or chassis 22 surrounded by a housing, casing or enclosure 24, typically made of a plastic material. Sheets of print media are fed through a printzone 25 by a print media handling system 26. The print media may be any type of suitable material, such as paper, card-stock, transparencies, photographic paper, fabric, metalized media, and the like. Print media handling system 26 has an input supply feed tray 28 for storing sheets of print media before printing. A series of conventional print media drive rollers (not shown) driven by a direct current (dc) motor and drive gear assembly (both of which are not shown) may be used to move the print media from feed tray 28, through printzone 25, and, after printing, onto a pair of extended output drying wing members 30, shown in a retracted or rest position in FIG. 1. Wings 30 momentarily hold a newly printed sheet of print media above any previously printed sheets still drying in an output tray portion 32, then wings 30 retract to the sides to drop the newly printed sheet into output tray 32. Print media handling system 26 may include a series of adjustment mechanisms for accommodating different sizes of print media, including letter, legal, A-4, envelopes, etc., such as a sliding length adjustment lever 34, a sliding width adjustment lever 36, and an envelope feed port 38. Although not shown, it is to be understood that print media handling system 26 may also include other items such as one or more additional print media feed trays. Additionally, media handling system 26 and printing device 20 may be configured to support specific printing tasks such as duplex printing (i.e., printing on both sides of a sheet of print media) and banner printing.

Printing device 20 also has a printer controller 40, illustrated schematically as a microprocessor, that receives instructions from a host device, typically a computer, such as a personal computer (not shown). Many of the printer controller functions may be performed by the host computer, including any printing device drivers resident on the host computer, by electronics on board the printer, or by interactions between the host computer and the electronics. As used herein, the term "printer controller 40" encompasses these functions, whether performed by the host computer, the printer, an intermediary device between the host computer and printer, or by combined interaction of such elements. Printer controller 40 may also operate in response to user inputs provided through a key pad 42 located on the exterior of the casing 24. A monitor (not shown) coupled to the computer host may be used to display visual information to an operator, such as the printer status or a particular program being run on the host computer. Personal computers, input devices, such as a keyboard and/or a mouse device, and monitors are all well known to those skilled in the art.

A carriage guide rod 44 is supported by chassis 22 to slidably support an off-axis inkjet pen carriage system 45 for travel back and forth across printzone 25 along a scanning axis 46. As can be seen in FIG. 1, scanning axis 46 is substantially parallel to an X-axis of the XYZ coordinate system shown in FIG. 1. It should be noted that the use of the word substantially in this document is used to account for things such as engineering and manufacturing tolerances, as well as variations not affecting performance of the present invention. Carriage 45 is also propelled along guide rod 44 into a servicing region, as indicated generally by arrow 48, located within the interior of housing 24. A conventional carriage drive gear and dc (direct current) motor assembly (both of which are not shown) may be coupled to drive an endless loop, which may be secured in a conventional manner to carriage 45, with the dc motor operating in response to control signals received from controller 40 to incrementally advance carriage 45 along guide rod 44 in response to rotation of the dc motor.

In printzone 25, a print media sheet receives ink from an inkjet cartridge, such as black ink cartridge 50 and three monochrome color ink cartridges 52, 54, and 56. Cartridges 50, 52, 54, and 56 are also often called "pens" by those in the art. Pens 50, 52, 54, and 56 each include small reservoirs for storing a supply of printing composition, referred to generally herein as "ink" in what is known as an "off-axis" ink delivery system, which is in contrast to a replaceable ink cartridge system where each pen has a reservoir that carries the entire ink supply as the printhead reciprocates over printzone 25 along scan axis 46. The replaceable ink cartridge system may be considered an "on-axis" system, whereas systems which store the main ink supply at a stationary location remote from the printzone scanning axis are called "off-axis" systems. It should be noted that the present invention is operable in both off-axis and on-axis systems.

In the illustrated off-axis printer 20, ink of each color for each printhead is delivered via a conduit or tubing system 58 from a group of main ink reservoirs 60, 62, 64, and 66 to the on-board reservoirs of respective pens 50, 52, 54, and 56.

Stationary ink reservoirs 60, 62, 64, and 66 are replaceable ink supplies stored in a receptacle 68 supported by printer chassis 22. Each of pens 50, 52, 54, and 56 has a respective printhead, as generally indicated by arrows 70, 72, 74, and 76, which selectively ejects ink to from an image on a sheet of print media in printzone 25.

Printheads 70, 72, 74, and 76 each have an orifice plate with a plurality of nozzles formed therethrough in a manner well known to those skilled in the art. The illustrated printheads 70, 72, 74, and 76 are thermal inkjet printheads, although other types of printheads may be used, such as piezoelectric printheads. Thermal printheads 70, 72, 74, and 76 typically include a plurality of resistors which are associated with the nozzles. Upon energizing a selected resistor, a bubble of gas is formed which ejects a droplet of ink from the nozzle onto a sheet of print media in printzone 25 under the nozzle. The printhead resistors are selectively energized in response to firing command control signals delivered by a multi-conductor strip 78 (a portion of which is shown in FIG. 1) from the controller 40 to printhead carriage 45.

To provide carriage positional feedback information to printer controller 40, a conventional optical encoder strip 84 extends along the length of the printzone 25 and over service station area 48, with a conventional optical encoder reader being mounted on a back surface of printhead carriage 45 to read positional information provided by encoder strip 84. Printer 20 uses optical encoder strip 84 and the optical encoder reader (not shown) to trigger the firing of printheads 70, 72, 74, and 76, as well as to provide feedback for position and velocity of carriage 45. Optical encoder strip 84 may be made from things such as photo imaged MYLAR brand film, and works with a light source and a light detector (both of which are not shown) of the optical encoder reader. The light source directs light through strip 84 which is received by the light detector and converted into an electrical signal which is used by controller 40 of printing device 20 to control firing of printheads 70, 72, 74, and 76, as well as carriage 45 position and velocity. Markings or indicia on encoder strip 84 periodically block this light from the light detector in a predetermined manner which results in a corresponding change in the electrical signal from the detector. The manner of providing positional feedback information via optical encoder reader may be accomplished in a variety of different ways known to those skilled in the art.

In order for the image to be fixed to the print media so that it will not smear, the ink must be dried. The ink is dried by a combination of the solvent evaporating and the solvent absorbing into the print medium both of which take time. Various factors control the amount of time required for a particular ink to dry. These factors include the type of print media, the quantity of solvent in an ink, the amount of ink on the print media, and ambient temperature and humidity. To reduce the amount of this time, the surface of some types of print media may be specially coated to help speed drying. Other means may also be used such as special chemicals generally know as "fixers" that are applied to print media before or after printing. Various types of heating devices may also be used to heat print media before and/or after printing.

Irrespective of how drying is accomplished, it is useful to know printing composition dry time for a particular combination of printing composition, print medium, printing device, and ambient conditions. Such information can be used by printing device 20 to help prevent image smear, print media cockle (print media buckle toward a printhead), and print media curl (curling along at least one edge of a print media), as well as help maximize printing device 20 throughput.

Accordingly, the present invention is directed to measuring printing composition dry time to help prevent the above-described problems and optimize printing. The present invention accomplishes this without degrading output print quality of printing device 20.

An embodiment of an optical detection system 86 constructed in accordance with the present invention is attached to bottom 88 of carriage 45. Detection system 86 is coupled to controller 40 so that controller 40 can receive information from detection system 86. As discussed more fully below, detection system 86 is scanned across printing composition subsequent to deposition of the printing composition onto a print medium. During such scanning, detection system 86 illuminates the printing composition and measures, over a selected period of time, a quantity of light reflected by the printing composition in response to such illumination. The dry time for the printing composition is then determined. This determination may be made by controller 40, by a computing device of detection system 86, referred to herein as a controller, or by a combination of the two.

Figure 2:
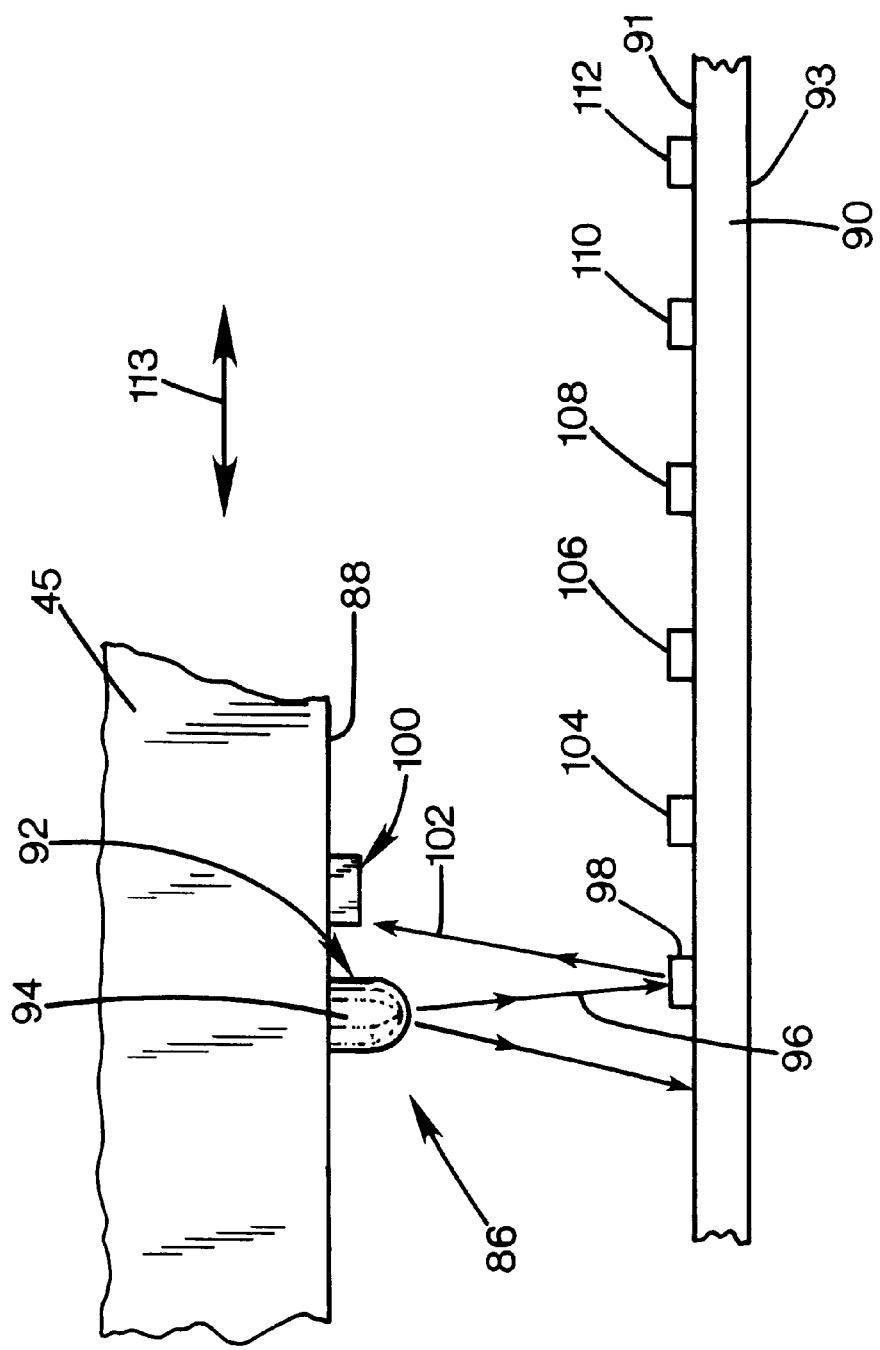
FIG. 2 is a diagrammatic illustration of a detection system in accordance with the present invention optically scanning drying printing composition on a sheet of print media in accordance with the present invention.

A diagrammatic illustration of detection system 86 optically scanning a print medium 90 is shown in FIG. 2. As can be seen in FIG. 2, detection system 86 includes a source 92, here shown as a light emitting diode (LED) 94. Source 92 is configured to transmit a first light signal 96 toward wet printing composition 98, 104, 106, 108, 110, and 112 deposited on a first surface 91 of print medium 90 by one or more of pens 50, 52, 54, and 56. In this case, printing composition 98, 104, 106, 108, 110, and 112 is composed of one or more drops of ink deposited by one or more of pens 50, 52, 54, and 56. Each of these drops may have a volume substantially equal to a selected volume for pens 50, 52, 54, and 56. Although not shown, it is to be understood that printing composition may be deposited onto second surface 93 of print medium 90 as well through the use of, for example, a duplexing unit (not shown).

Detection system 86 also includes a sensor 100 configured to detect a second light signal 102 reflected by printing composition 98, 104, 106, 108, 110, and 112 in response to illumination by first light signal 96. Second light signal 102 has a magnitude that decreases to a substantially constant value as printing composition 98, 104, 106, 108, 110, and 112 dries over a period of time. Sensor 100 is also configured to convert detected second light signal 102 into an electrical signal having a value proportional to the magnitude of light signal 102, as more fully discussed below. A controller of detection system 86 and/or controller 40 are coupled to sensor 100 and receive the electrical signal from sensor 100 over the period of time printing composition 98, 104, 106, 108, 110, and 112 dries. From this electrical signal, the controller determines the dry time for printing composition 98, 104, 106, 108, 110, and 112.

As generally illustrated by double-headed arrow 113 in FIG. 2, detection system 86 may be optically scanned bi-directionally across drying printing composition 98, 104, 106, 108, 110, 112 on first surface 91 of print medium 90 any number of times by translating carriage 45 along guide rod 44, as discussed above in connection with FIG. 1. Detection system 86 may also be positioned at a fixed point with respect to any of printing composition 98, 104, 106, 108, 110, 112 while printing composition 98, 104, 106, 108, 110, 112 dries.

Figure 3:
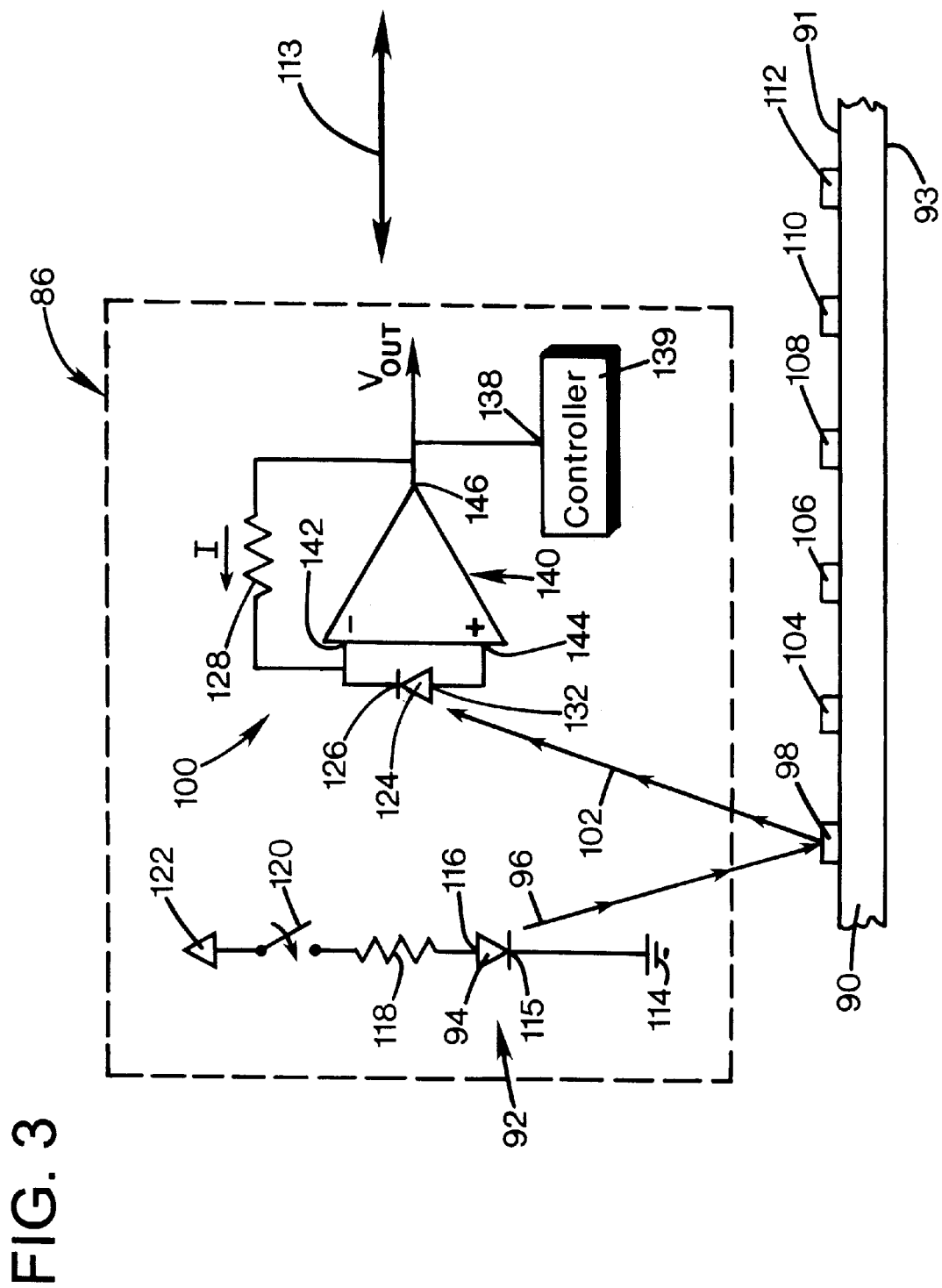
FIG. 3 is a schematic diagram of the detection system shown in FIG. 1 optically scanning drying printing composition on a sheet of print media in accordance with the present invention.

A schematic diagram of source 92 and sensor 100 of detection system 86 optically scanning drying printing composition 98, 104, 106, 108, 110, and 112 on print medium 90 in accordance with the present invention is shown in FIG. 3.

As noted above, source 92 includes a light emitting diode (LED) 94 having a cathode 115 electrically connected to ground 114 and an anode 116 electrically connected to a current limiting resistor 118. Current limiting resistor 118 is also electrically connected to a switch 120 that is electrically connected to a power source 122. When switch 120 is closed, as, for example, when a sheet of print media is removed from input supply feed tray 28 to printzone 25 by print media handling system 26 (i.e., "picked"), power is supplied to LED 94 via power source 122 to produce first light signal 96. When switch 120 is open, no power is supplied to LED 94 and, as a consequence, no first light signal 96 is produced. Switch 120 is configured to be normally open so no first light signal 96 is produced. Switch 120 may be closed during "picking" of a sheet of print media by, for example, controller 40. Alternatively, switch 120 may be positioned in input supply feed tray 28 so that it closes during "picking" by physical contact between switch 120 and the "picked" sheet of print media.

As can also be seen in FIG. 3, sensor 100 includes a photodiode 124 having a cathode 126 electrically connected to an inverting input 142 of an amplifier 140 and also to a feedback resistor 128. Photodiode 124 also has an anode 132 electrically connected to a noninverting input 144 of amplifier 140. Feedback resistor 128 is also electrically connected to output 146 of amplifier 140. Output 146 of amplifier 140 is coupled to input 138 of a controller 139 or, in alternative embodiments of detection system 86 of the present invention, an input of controller 40. This controller determines printing composition dry time based upon the changing value of $V_{OUT}$ at output 146 of inverting amplifier 140, as more fully discussed below.

In operation, photodiode 124 is configured to conduct current through feedback resistor 128, generally represented as a current I, as second light signal 102 illuminates photodiode 124. This current (I) produces an electrical signal at output 146 of amplifier 140, generally represented as a voltage $V_{OUT}$, that is received at input 138 of controller 139 or an input of controller 40. The resistance of photodiode 124 is configured to increase when the magnitude of second light signal 102 illuminating it decreases as printing composition 98, 104, 106, 108, 110, and 112 dries. As the resistance of photodiode 124 increases, the amount of current (I) decreases. As the current (I) decreases, $V_{OUT}$ also decreases.

Once printing composition 98, 104, 106, 108, 110, and 112 is dry, the value of current (I) through feedback resistor stabilizes to a substantially constant final value, producing a substantially constant final value for $V_{OUT}$. The amount of dry time for printing composition may be determined by measuring the amount of time required for $V_{OUT}$ to decrease from its initial maximum value when printing composition 98, 104, 106, 108, 110, and 112 is initially deposited on first surface 91 of print medium 90 to a stabilized substantially constant final value when printing composition 98, 104, 106, 108, 110, and 112 is dry.

As discussed above, knowing printing composition dry time is useful in controlling operation of printing device 20. For example, such information can be used by printing device 20 to help prevent image smear, print media cockle, and print media curl, as well as help maximize printing device throughput.

Although the invention has been described and illustrated in detail, it is to be clearly understood that the same is intended by way of illustration and example only, and is not to be taken necessarily, unless otherwise stated, as an express limitation. For example, in one or more alternative embodiments of the present, photodiode 124 may be replaced with a phototransistor. The spirit and scope of the present invention are to be limited only by the terms of the following claims.

What is claimed is:

1. A detection system for measuring a dry time of a printing composition used by a printing device, the detection system comprising:
   a source configured to transmit a first light signal toward a quantity of printing composition deposited on a print medium, the printing composition reflecting a second light signal in response to illumination by the first light signal, the second light signal having a magnitude that decreases to a substantially constant value as the printing composition dries over a period of time;
   a sensor configured to detect the second light signal and convert the second light signal into an electrical signal having a value proportional to the magnitude of the second light signal; and
   a controller coupled to the sensor, the controller configured to receive the electrical signal from the sensor over the period of time the printing composition dries and determine a dry time for the printing composition based upon the electrical signal.

2. The detection system of claim 1, wherein the controller is further configured to adjust an operating parameter of the printing device based upon the determined dry time.

3. The detection system of claim 1, wherein the source includes a light emitting diode and the sensor includes a photodiode.

4. A printing device comprising the detection system as recited in claim 1.

5. A detection system for measuring a dry time of a printing composition used by a printing device, the detection system comprising:
   means for illuminating a printing composition subsequent to deposition on a print medium;
   means for measuring over a selected period of time a quantity of light reflected by the printing composition subsequent to illumination; and
   means for determining a dry time for the printing composition based upon the measured quantity of light reflected by the printing composition over the selected period of time.

6. The detection system of claim 5, further comprising means for adjusting at least one operating parameter of a printing device based upon the dry time.

7. The detection system of claim 5, further comprising means for depositing the printing composition on the print medium.

8. The detection system of claim 7, wherein the depositing means comprising an inkjet printhead.

9. A printing device comprising the detection system as recited in claim 5.

10. A method of measuring a dry time of a printing composition used by a printing device, the method comprising:
    depositing a quantity of printing composition onto a print medium;
    illuminating the printing composition subsequent to printing;
    measuring over a selected period of time a quantity of light reflected by the printing composition in response to illuminating; and
    determining a dry time for the printing composition based upon the measured quantity of light reflected by the printing composition over the selected period of time.

11. The method of claim 10, wherein depositing comprises placing a plurality of drops of printing composition onto the print medium.

12. The method of claim 11, wherein depositing comprises selecting a number of drops of printing composition to place onto the print medium.

13. The method of claim 11, wherein each of the drops has a volume substantially equal to a selected volume.

14. The method of claim 10, further comprising adjusting at least one operating parameter of a printing device based upon the determined dry time.

15. The method of claim 10, wherein illuminating and measuring comprise optically scanning the printing composition.

* * * * *